(12) United States Patent
Wu

(10) Patent No.: US 7,062,798 B2
(45) Date of Patent: Jun. 20, 2006

(54) GLASSES HAVING A PROTECTIVE MODULE

(76) Inventor: Wen-Hsiung Wu, 58, Ma Yuan West St., Taichung (TW)

( * ) Notice: Subject to any disclaimer, the term of this patent is extended or adjusted under 35 U.S.C. 154(b) by 280 days.

(21) Appl. No.: 10/724,333

(22) Filed: Nov. 25, 2003

(65) Prior Publication Data

US 2005/0108812 A1    May 26, 2005

(51) Int. Cl.
*A61F 9/02* (2006.01)

(52) U.S. Cl. .......................................................... 2/448

(58) Field of Classification Search .................... 2/426, 2/439, 448, 428, 429; 351/83, 86, 43
See application file for complete search history.

(56) References Cited

U.S. PATENT DOCUMENTS

| | | | | |
|---|---|---|---|---|
| 3,896,496 A | * | 7/1975 | Leblanc et al. ............... | 2/439 |
| 5,682,621 A | * | 11/1997 | Park .............................. | 2/441 |
| 6,694,532 B1 | * | 2/2004 | Chen ............................. | 2/428 |
| 6,804,835 B1 | * | 10/2004 | Chou ............................ | 2/436 |
| 6,848,786 B1 | * | 2/2005 | Teng ........................... | 351/83 |
| 6,865,753 B1 | * | 3/2005 | Nishida ........................ | 2/426 |
| 2003/0037367 A1 | * | 2/2003 | Fukasawa ..................... | 2/428 |

* cited by examiner

*Primary Examiner*—Katherine M. Moran
(74) *Attorney, Agent, or Firm*—Alan D. Kamrath; Nikolai & Mersereau, P.A.

(57) ABSTRACT

A pair of glasses include a rim having two opposite sides each formed with a receiving hole having a periphery formed with an urging face directed outward in an oblique manner, and a protective module selectively mounted on the rim and including a protective frame mounted on an inner side of the rim and having two opposite sides each formed with a snapping portion forced into the receiving hole of the rim and urged on the urging face of the receiving hole of the rim, so that the protective frame is secured on the rim. Thus, the protective module is combined with the rim rigidly and stably so that the glasses can provide a protective function to the user.

9 Claims, 4 Drawing Sheets

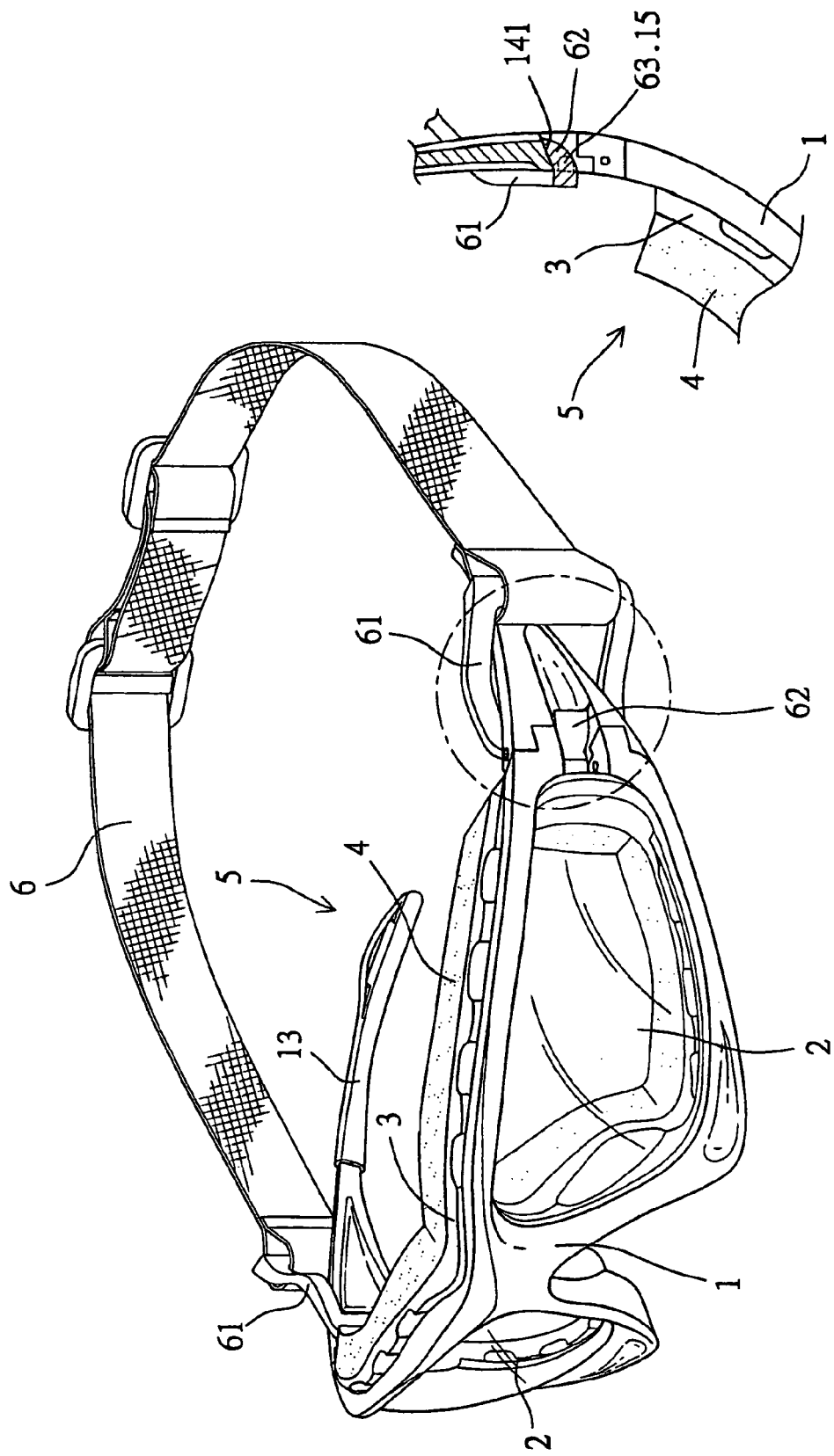

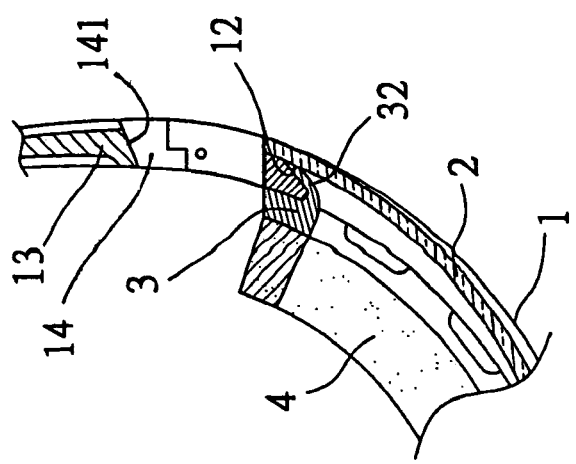
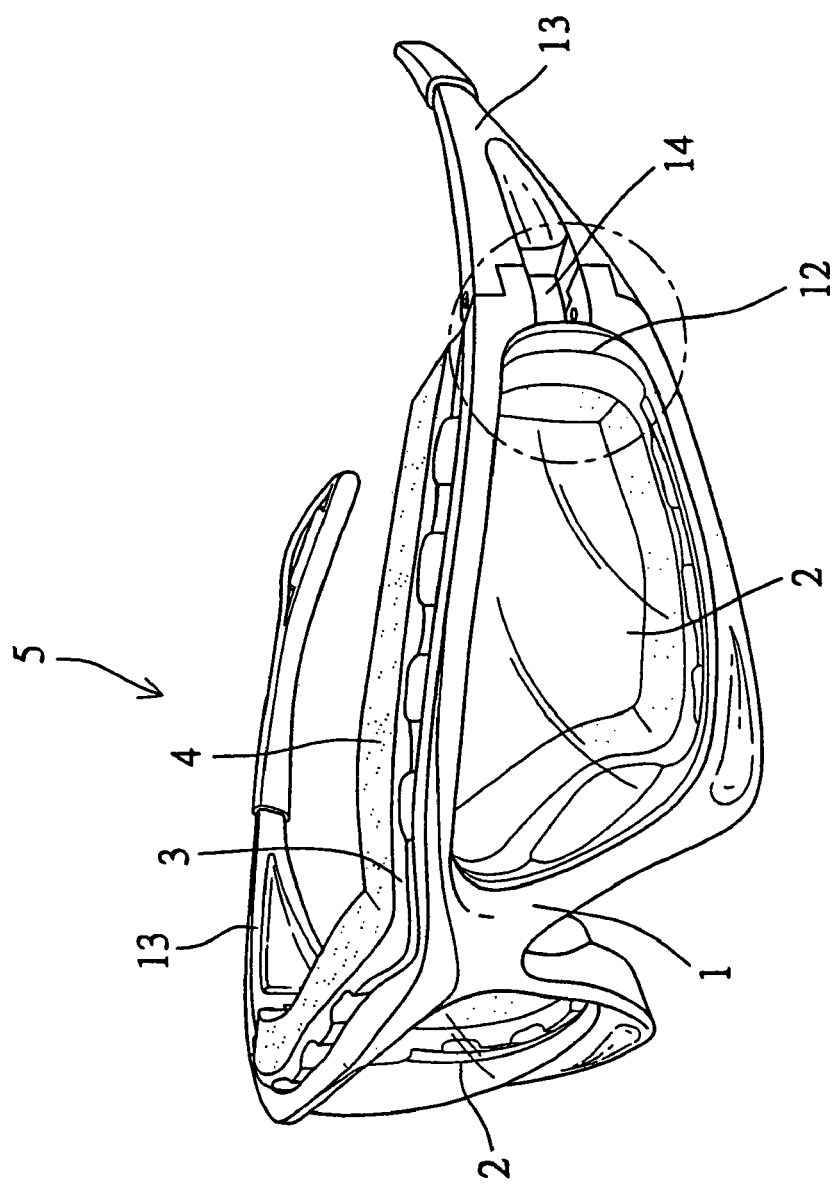

GLASSES HAVING A PROTECTIVE MODULE

BACKGROUND OF THE INVENTION

1. Field of the Invention

The present invention relates to a pair of glasses, and more particularly to a pair of glasses having a protective module that is assembled and dismantled easily and conveniently.

2. Description of the Related Art

A conventional pair of glasses 10 in accordance with the prior art shown in FIG. 6 comprises a rim 20 provided with two lenses 30 and formed with a plurality of screw bores 201, a protective frame 50 mounted on an inner side of the rim 20 and formed with a plurality of through holes 501, a plurality of screw members 60 each extended through a respective one of the through holes 501 of the protective frame 50 and each screwed into a respective one of the screw bores 201 of the rim 20, and two protective strips 40 each bonded on an inner side of the protective frame 50. However, it is necessary to bond the two protective strips 40 on the inner side of the protective frame 50 and to combine the rim 20 with the protective frame 50 by the screw members 60, thereby causing inconvenience in assembly, and thereby increasing costs of fabrication.

SUMMARY OF THE INVENTION

The primary objective of the present invention is to provide a pair of glasses having a protective module that is assembled and dismantled easily and conveniently.

Another objective of the present invention is to provide a pair of glasses, wherein the protective module is combined with the rim rigidly and stably so that the glasses can provide a protective function to the user.

A further objective of the present invention is to provide a pair of glasses, wherein the fastening strap is mounted on the rim rigidly and stably, so that the glasses are available for sport.

In accordance with the present invention, there is provided a pair of glasses, comprising:

a rim having two opposite sides each formed with a receiving hole having a periphery formed with an urging face directed outward in an oblique manner; and a protective module selectively mounted on the rim and including a protective frame mounted on an inner side of the rim and having two opposite sides each formed with a snapping portion forced into the receiving hole of the rim and urged on the urging face of the receiving hole of the rim, so that the protective frame is secured on the rim.

Further benefits and advantages of the present invention will become apparent after a careful reading of the detailed description with appropriate reference to the accompanying drawings.

BRIEF DESCRIPTION OF THE DRAWINGS

FIG. 1 is a perspective view of a pair of glasses in accordance with the preferred embodiment of the present invention;

FIG. 2 is a partially cut-away plan cross-sectional view of the glasses as shown in FIG. 1;

FIG. 4 is a partially perspective assembly view of the in accordance with the preferred embodiment of the present invention;

FIG. 5 is a partially cut-away plan cross-sectional view of the glasses as shown in FIG. 4.

DETAILED DESCRIPTION OF THE INVENTION

Figure 3:
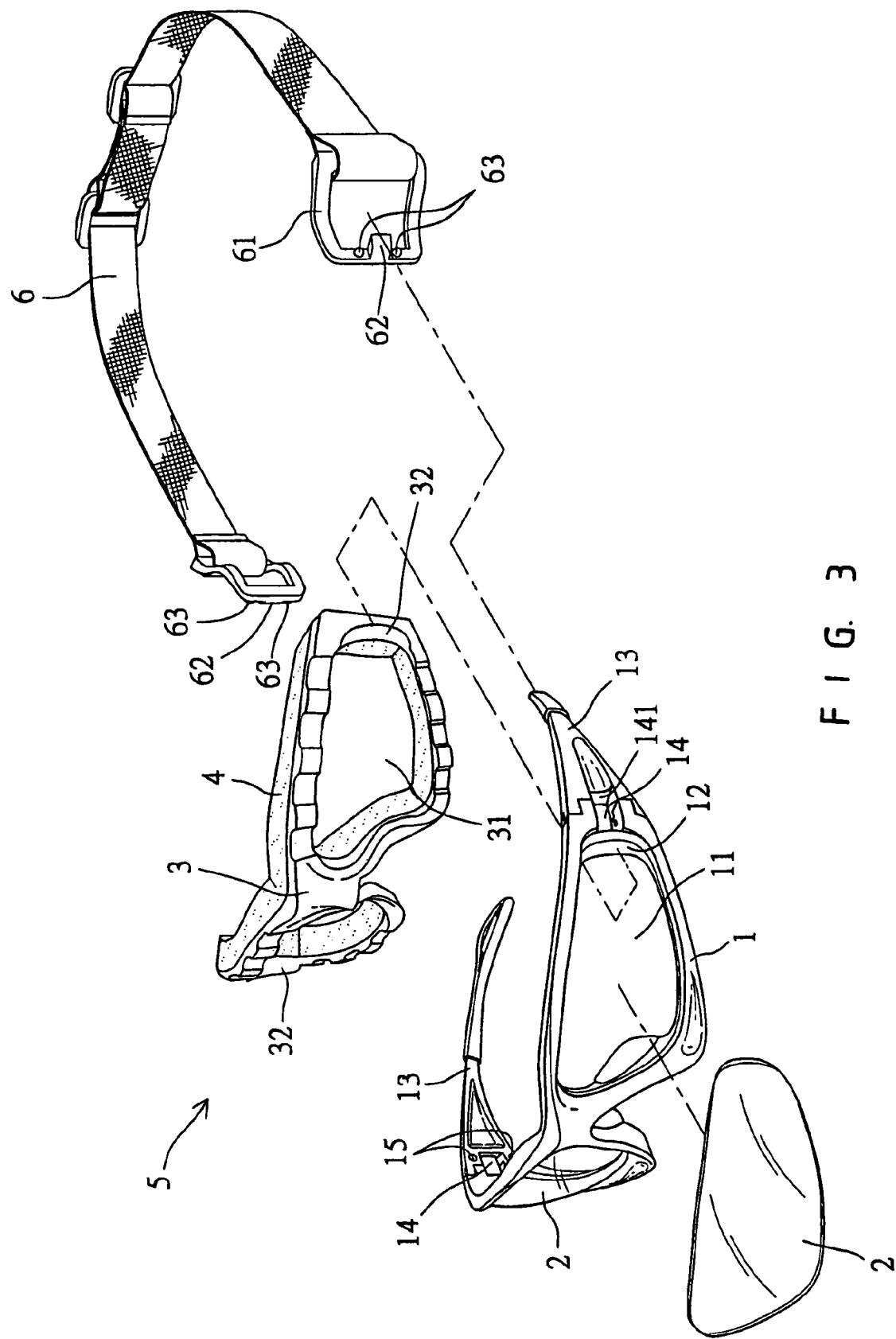
FIG. 3 is an exploded perspective view of the glasses as shown in FIG. 1.
Figure 6:
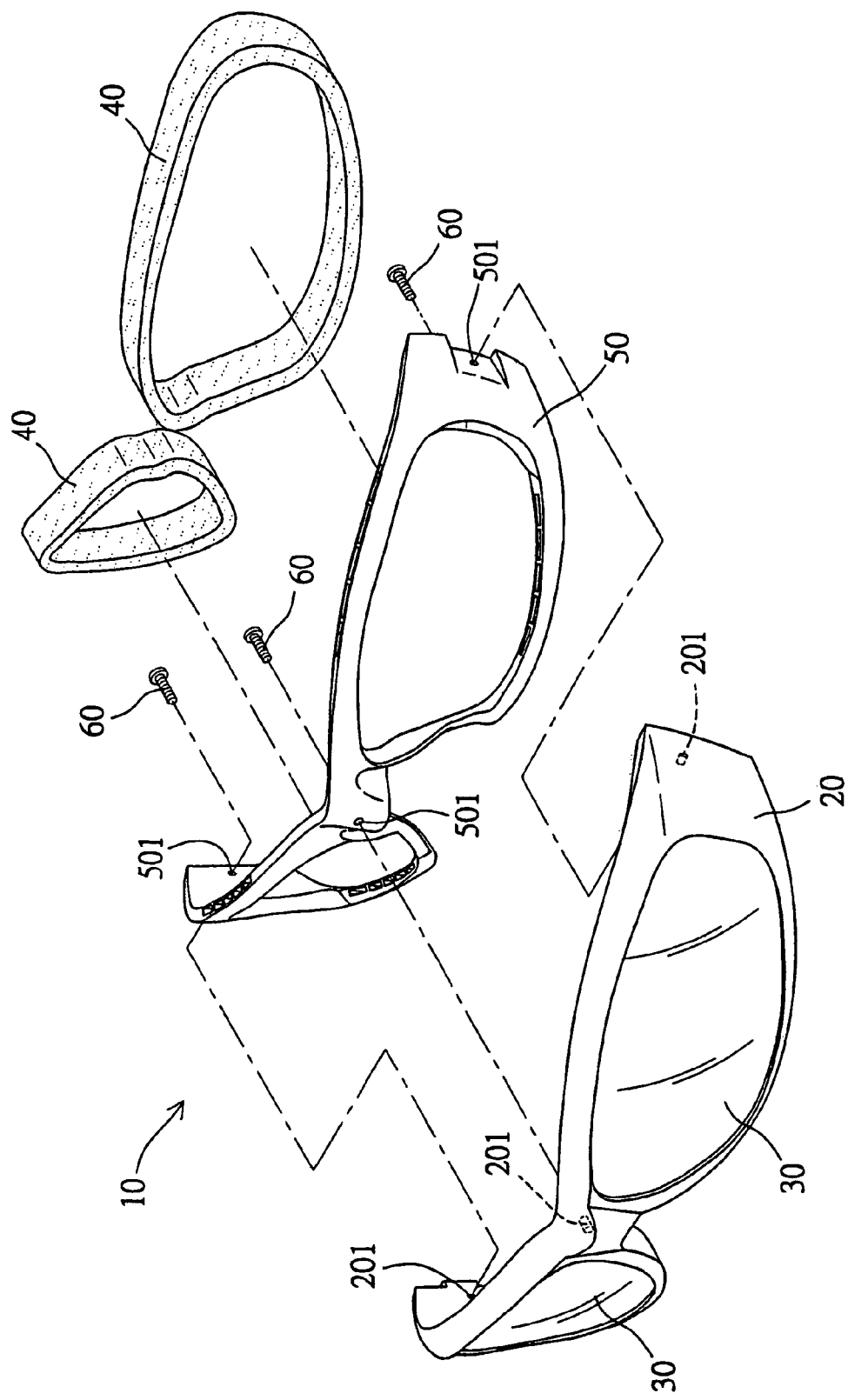
FIG. 6 is an exploded perspective view of a conventional pair of glasses in accordance with the prior art.

Referring to the drawings and initially to FIGS. 1–3, a pair of glasses in accordance with the preferred embodiment of the present invention comprises a rim 1, a protective module 5, and a fastening strap 6.

The rim 1 has two opposite sides each formed with a receiving hole 11 having a periphery formed with an urging face 12 directed outward in an oblique manner. The glasses further comprises two lenses 2 each mounted in the respective receiving hole 11 of the rim 1.

The glasses further comprises two temples 13 each pivotally mounted on a respective one of the two opposite sides of the rim 1 and each formed with a positioning hole 14 having a side formed with an inclined face 141. Each of the two temples 13 has an inner face formed with two locking holes 15 (see FIG. 2).

The protective module 5 is selectively mounted on the rim 1 and includes a protective frame 3 mounted on an inner side of the rim 1, and a protective strip 4 mounted on a periphery of the protective frame 3.

The protective frame 3 is made of a flexible material and has a shape mating with that of the rim 1. The protective frame 3 has two opposite sides each formed with a snapping portion 32 forced into the receiving hole 11 of the rim 1 and urged on the urging face 12 of the receiving hole 11 of the rim 1, so that the protective frame 3 is secured on the rim 1. The snapping portion 32 of the protective frame 3 is directed outward in an oblique manner. Each of the two opposite sides of the protective frame 3 is formed with a through hole 31 aligning with the receiving hole 11 of the rim 1.

The protective strip 4 is made of a soft material and has a shape mating with that of the protective frame 3.

The fastening strap 6 is selectively mounted on the rim 1 and rested on the two temples 13. The fastening strap 6 has two ends each provided with a hollow connecting member 61 mounted on a respective one of the two temples 13. The connecting member 61 of the fastening strap 6 has a side formed with a locking hook 62 locked in the positioning hole 14 of the respective temple 13 and urged on the inclined face 141 of the positioning hole 14 of the respective temple 13. The connecting member 61 of the fastening strap 6 is formed with two locking bosses 63 each located beside the locking hook 62 and each locked in a respective one of the two locking holes 15 of the respective temple 13.

In assembly, referring to FIGS. 4 and 5, the snapping portion 32 of the protective frame 3 is forced into the receiving hole 11 of the rim 1 and urged on the urging face 12 of the receiving hole 11 of the rim 1, so that the protective frame 3 is secured on the rim 1. Thus, the protective module 5 is combined with the rim 1 rigidly and stably so that the glasses can provide a protective function to the user.

In addition, the user can exert an external force on the two opposite sides of the protective frame 3 to release the snapping portion 32 of the protective frame 3 from the urging face 12 of the receiving hole 11 of the rim 1, so that the protective frame 3 detached from the rim 1, thereby detaching the protective module 5 from the rim 1. Thus, the glasses can function as common glasses.

Alternatively, as shown in FIGS. 1–3, when the connecting member 61 of the fastening strap 6 is mounted on a respective one of the two temples 13, the locking hook 62 of the connecting member 61 of the fastening strap 6 is locked in the positioning hole 14 of the respective temple 13 and urged on the inclined face 141 of the positioning hole 14 of the respective temple 13, while each of the two locking bosses 63 of the connecting member 61 of the fastening strap 6 is locked in a respective one of the two locking holes 15 of the respective temple 13, so that the fastening strap 6 is mounted on the rim 1 rigidly and stably. Thus, the glasses are available for sport.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

What is claimed is:

1. A pair of glasses, comprising:
    a rim having two opposite sides each formed with a receiving hole having a periphery formed with an urging face directed outward in an oblique manner; and
    a protective module mounted on the rim and including a protective frame mounted on an inner side of the rim and having two opposite sides each formed with a snapping portion forced into the receiving hole of the rim and urged on the urging face of the receiving hole of the rim, so that the protective frame is secured on the rim;
    two temples each pivotally mounted on a respective one of the two opposite sides of the rim, and a fastening strap mounted on the rim and rested on the two temples; wherein
    the fastening strap has two ends each provided with a hollow connecting member mounted on a respective one of the two temples;
    each of the two temples is formed with a positioning hole having a side formed with an inclined face, and the connecting member of the fastening strap has a side formed with a locking hook locked in the positioning hole of the respective temple and urged on the inclined face of the positioning hole of the respective temple.

2. The glasses in accordance with claim 1, further comprising two lenses each mounted in the respective receiving hole of the rim.

3. The glasses in accordance with claim 1, wherein the protective module further includes a protective strip mounted on a periphery of the protective frame.

4. The glasses in accordance with claim 1, wherein the protective frame is made of a flexible material.

5. The glasses in accordance with claim 1, wherein the protective frame has a shape mating with that of the rim.

6. The glasses in accordance with claim 1, wherein the snapping portion of the protective frame is directed outward in an oblique manner.

7. The glasses in accordance with claim 1, wherein each of the two opposite sides of the protective frame is formed with a through hole aligning with the receiving hole of the rim.

8. The glasses in accordance with claim 1, wherein the protective strip is made of a soft material and has a shape mating with that of the protective frame.

9. The glasses in accordance with claim 1, wherein each of the two temples has an inner face formed with two locking holes, and the connecting member of the fastening strap is formed with two locking bosses each located beside the locking hook and each locked in a respective one of the two locking holes of the respective temple.

* * * * *